United States Patent
Ihn et al.

(10) Patent No.: US 8,290,719 B2
(45) Date of Patent: Oct. 16, 2012

(54) MODE IDENTIFICATION AND DECOMPOSITION FOR ULTRASONIC SIGNALS

(75) Inventors: Jeong-Beom Ihn, Bellevue, WA (US); Christopher J. Martens, Creve Coeur, MO (US)

(73) Assignee: The Boeing Company, Chicago, IL (US)

( * ) Notice: Subject to any disclaimer, the term of this patent is extended or adjusted under 35 U.S.C. 154(b) by 451 days.

(21) Appl. No.: 12/239,144

(22) Filed: Sep. 26, 2008

(65) Prior Publication Data
US 2010/0079258 A1    Apr. 1, 2010

(51) Int. Cl.
G01B 5/28    (2006.01)
G01B 5/30    (2006.01)

(52) U.S. Cl. ........... 702/36; 702/35; 702/39; 702/54; 702/56; 702/59; 702/189; 702/190

(58) Field of Classification Search ............ 702/35, 702/36, 39, 48, 54, 56, 57, 59, 75, 79, 89, 702/90, 91, 94, 103, 104, 119, 142, 171, 702/183, 185, 189, 190
See application file for complete search history.

(56) References Cited

U.S. PATENT DOCUMENTS

| 4,931,965 A * | 6/1990 | Kaneko et al. ............... 345/174 |
| 6,360,609 B1 * | 3/2002 | Wooh ............................ 73/602 |
| 6,581,014 B2 | 6/2003 | Sills et al. |
| 6,950,493 B2 | 9/2005 | Besson |
| 7,590,510 B2 * | 9/2009 | Kim ............................. 702/183 |
| 7,602,963 B2 * | 10/2009 | Nightingale et al. ......... 382/149 |
| 2009/0150094 A1 * | 6/2009 | Van Velsor et al. ............ 702/39 |

OTHER PUBLICATIONS

Michaels J E, "Detection, localization and characterization of damage in plates with an in situ aray of spatially distributed ultrasonic sensors", May 14, 2008, IOP Publishing LTD, Smart Materials and Structures 17 (2008) 035035, pp. 1-15.*

* cited by examiner

Primary Examiner — Michael Nghiem
Assistant Examiner — Yaritza H Perez Bermudez
(74) Attorney, Agent, or Firm — Yee & Associates, P.C

(57) ABSTRACT

A method is present for processing a signal. A response signal is received from a structure. The response signal is decomposed into a plurality of signals based on a number of characteristics. A mode in the plurality of signals is identified based on a number of known characteristics for the mode, wherein the mode has a velocity.

18 Claims, 7 Drawing Sheets

MODE IDENTIFICATION AND DECOMPOSITION FOR ULTRASONIC SIGNALS

BACKGROUND INFORMATION

1. Field

The present disclosure relates generally to processing data and in particular to processing data from responses of a structure to an input waveform. Still more particularly, the present disclosure relates to a method, apparatus, and computer usable program code for identifying modes within a response signal received from a structure.

2. Background

Composite and metallic aircraft structures may be susceptible to internal changes that may occur from fatigue, impacts, and other events or conditions. Composite materials typically have a minimal visual indication of these types of changes. As a result, an aircraft may be inspected to assess the integrity of the structure on a periodic basis or after visual indications of surface anomalies, such as dents and scratches.

For example, impacts to a structure, such as an aircraft, may occur during cargo loading and unloading. These types of impacts may warrant an inspection to determine whether changes or anomalies have occurred as a result of these impacts. Inspection of the structure of an aircraft may be time-consuming and costly in terms of the time and skill needed to perform the inspection. Further, an airline may incur lost revenues due to the aircraft being out of service.

Structural health monitoring techniques have been developed and used to monitor materials and structures. These techniques often build the health monitoring systems into the structures. These health monitoring systems may be used to determine whether changes have occurred to these materials and structures over time.

Sudden changes in environment, such as electromagnetic effects, mechanical stresses, and other environmental effects may affect the integrity of various materials and structures over time. By having health monitoring systems built into or associated with the structures to monitor the structures during use, appropriate measures and responses may be taken to prevent catastrophic failures and may prolong the lifespan of these structures.

The monitoring of structures may include various non-destructive elevation methods, such as ultrasonic testing or x-ray testing. Ultrasonic testing uses contact-based transducers to mechanically scan a structure. These distributed sensors and actuators may be surface mounted on the structure or may be embedded in the structure to generate and propagate diagnostic signals into the structure being monitored.

A structural health monitoring system is based on using a transmitter and sensor configuration to transmit waveforms at various frequency ranges and to acquire data from the responses. Oftentimes, a transducer may function both as a transmitter and a sensor. Structural health monitoring systems may be employed in structures as onboard or integrated systems for detecting and characterizing anomalies or changes that may require maintenance.

Currently used structural health monitoring systems may require data from a large number of sensors attached to or embedded within the structure. The number of sensors may be large in order to obtain the data needed to identify the location for an anomaly. Currently used structural health monitoring systems may perform triangulation in which coordinates or estimates of a location of an anomaly may be calculated from data obtained from a number of different sensors.

It would be desirable to reduce the number of sensors needed to obtain an estimate of a location of an anomaly within a structure. The reduction in the number of sensors may reduce weight and complexity for a structural health monitoring system.

Therefore, it would be advantageous to have a method and apparatus that overcomes one or more of the problems described above.

SUMMARY

In one advantageous embodiment, a method is present for processing a signal. A response signal is received from a structure. The response signal is decomposed into a plurality of signals based on a number of characteristics. A mode in the plurality of signals is identified based on a number of known characteristics for the mode, wherein the mode has a velocity.

In another advantageous embodiment, a method is present for processing a signal to estimate a location of an anomaly. A response signal is received from a structure and is generated in response to the signal being sent into the structure by a transducer. The response signal is separated into a plurality of data sets to form a data profile. A mode is identified to form an identified mode, wherein the identified mode comprises a data set and a known group velocity. The data set for the identified mode is fitted to the data profile to find a particular data set having a best fit to the identified mode. The location of the anomaly causing the response signal is estimated from a time delay of the particular data set and the known group velocity for the particular data set.

In yet another advantageous embodiment, an apparatus comprises a structure having a plurality of components, a number of transmitters, a number of sensors, and a structural health monitoring system. The number of transmitters is physically associated with the plurality of components and is capable of sending signals into the plurality of components. The number of sensors is capable of detecting responses to the signals. The structural health monitoring system is in communication with the number of transmitters and the number of sensors. The structural health monitoring system is capable of causing a transmitter in the number of transmitters to send a signal into a component within the plurality of components. The structural health monitoring system is capable of receiving a response signal generated in response to the signal. The structural health monitoring system is capable of decomposing the response signal into a plurality of signals based on a number of characteristics. The structural health monitoring system also is capable of identifying a mode within the plurality of signals based on a number of known characteristics for the mode, wherein the mode has a velocity.

In still yet another advantageous embodiment, a computer program product is present for processing a signal. The computer program product comprises a computer recordable storage medium and program code stored on the computer recordable storage medium. Program code is present for receiving a response signal from a structure. Program code is present for decomposing the response signal into a plurality of signals based on a number of characteristics. Program code is also present for identifying a mode in the plurality of signals based on a number of known characteristics for the mode, wherein the mode has a velocity.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
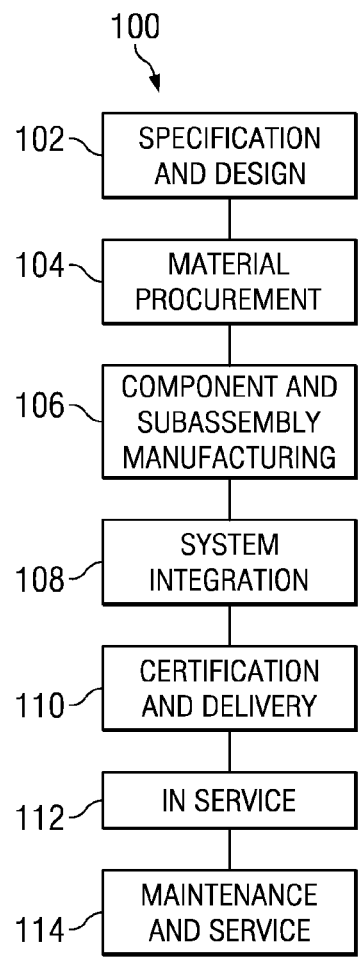
FIG. 1 is a diagram illustrating an aircraft manufacturing and service method in accordance with an advantageous embodiment.
Figure 2:
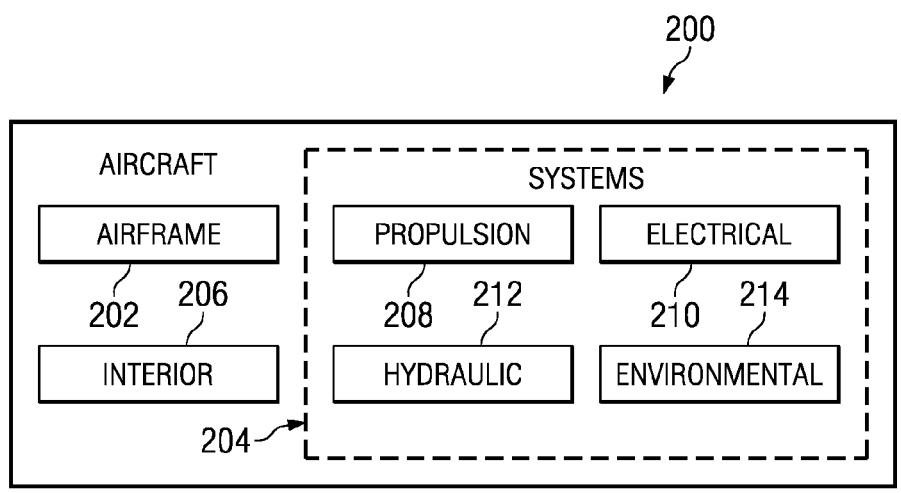
FIG. 2 is a diagram of an aircraft in which an advantageous embodiment may be implemented.

Referring more particularly to the drawings, embodiments of the disclosure may be described in the context of the aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced while aircraft 200 is in service 112 in FIG. 1.

Also, one or more apparatus embodiments, method embodiments, or a combination thereof may be utilized during production stages, such as component and subassembly manufacturing 106 and system integration 108 in FIG. 1, for example, without limitation, by substantially expediting the assembly of or reducing the cost of aircraft 200. Similarly, one or more of apparatus embodiments, method embodiments, or a combination thereof may be utilized while aircraft 200 is in service 112 or during maintenance and service 114 in FIG. 1.

In one illustrative example, health monitoring systems of the advantageous embodiments may be implemented during component and subassembly manufacturing 106 and during system integration 108. In other advantageous embodiments, health monitoring systems may be added or implemented during maintenance and service 114. In these different advantageous embodiments, these health monitoring systems may provide a capability to reduce the number of sensors needed to identify anomalies that may occur within structures such as, for example, airframe 202 in aircraft 200.

Figure 3:
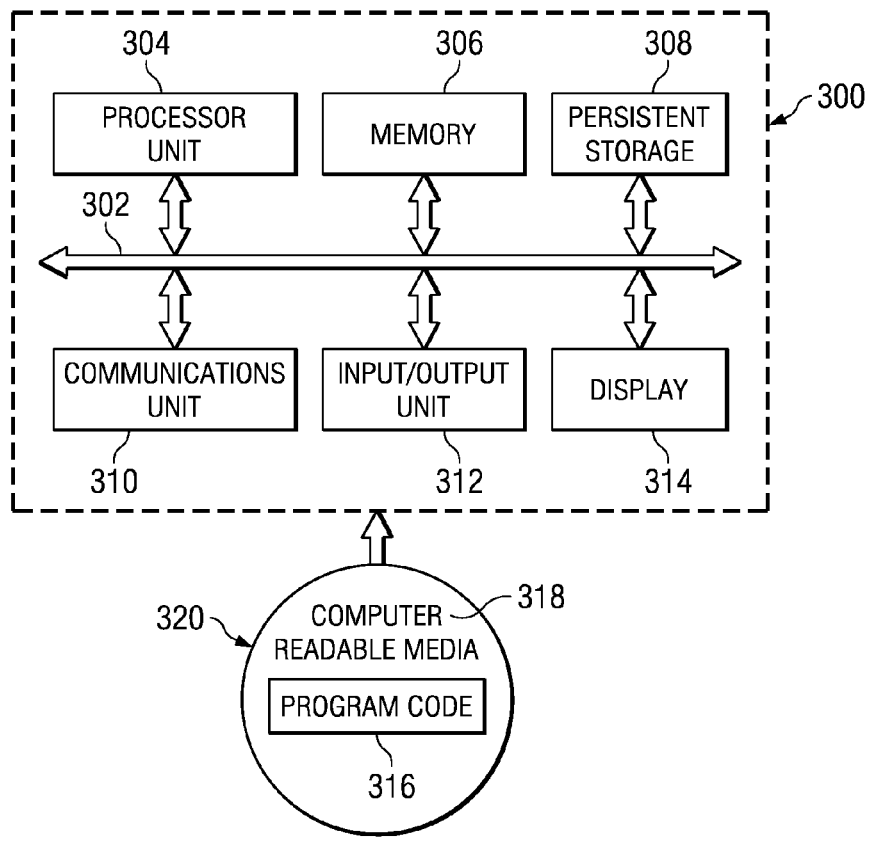
FIG. 3 is a diagram of a data processing system in accordance with an illustrative embodiment.

Turning now to FIG. 3, a diagram of a data processing system is depicted in accordance with an illustrative embodiment. In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a set of one or more processors or may be a multi-processor core, depending on the particular implementation. Further, processor unit 304 may be implemented using one or more heterogeneous processor systems in which a main processor is present with secondary processors on a single chip.

As another illustrative example, processor unit 304 may be a symmetric multi-processor system containing multiple processors of the same type.

Memory 306 and persistent storage 308 are examples of storage devices. A storage device is any piece of hardware that is capable of storing information either on a temporary basis and/or a permanent basis. Memory 306, in these examples, may be, for example, a random access memory or any other suitable volatile or non-volatile storage device.

Persistent storage 308 may take various forms depending on the particular implementation. For example, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communications links.

Input/output unit 312 allows for input and output of data with other devices that may be connected to data processing system 300. For example, input/output unit 312 may provide a connection for user input through a keyboard and mouse. Further, input/output unit 312 may send output to a printer. Display 314 provides a mechanism to display information to a user.

Instructions for the operating system and applications or programs are located on persistent storage 308. These instructions may be loaded into memory 306 for execution by processor unit 304. The processes of the different embodiments may be performed by processor unit 304 using computer implemented instructions, which may be located in a memory, such as memory 306.

These instructions are referred to as program code, computer usable program code, or computer readable program code that may be read and executed by a processor in processor unit 304. The program code in the different embodiments may be embodied on different physical or tangible computer readable media, such as memory 306 or persistent storage 308.

Program code 316 is located in a functional form on computer readable media 318 that is selectively removable and may be loaded onto or transferred to data processing system 300 for execution by processor unit 304. Program code 316 and computer readable media 318 form computer program product 320 in these examples.

In one example, computer readable media 318 may be in a tangible form, such as, for example, an optical or magnetic disc that is inserted or placed into a drive or other device that is part of persistent storage 308 for transfer onto a storage device, such as a hard drive that is part of persistent storage 308.

In a tangible form, computer readable media 318 also may take the form of a persistent storage, such as a hard drive, a thumb drive, or a flash memory that is connected to data processing system 300. The tangible form of computer readable media 318 is also referred to as computer recordable storage media. In some instances, computer readable media 318 may not be removable.

Alternatively, program code 316 may be transferred to data processing system 300 from computer readable media 318 through a communications link to communications unit 310 and/or through a connection to input/output unit 312. The communications link and/or the connection may be physical or wireless in the illustrative examples. The computer readable media also may take the form of non-tangible media, such as communications links or wireless transmissions containing the program code.

In some illustrative embodiments, program code 316 may be downloaded over a network to persistent storage 308 from another device or data processing system for use within data processing system 300. For instance, program code stored in a computer readable storage medium in a server data processing system may be downloaded over a network from the server to data processing system 300. The data processing system providing program code 316 may be a server computer, a client computer, or some other device capable of storing and transmitting program code 316.

The different components illustrated for data processing system 300 are not meant to provide architectural limitations to the manner in which different embodiments may be implemented. The different illustrative embodiments may be implemented in a data processing system including components in addition to or in place of those illustrated for data processing system 300.

Other components shown in FIG. 3 can be varied from the illustrative examples shown. The different embodiments may be implemented using any hardware device or system capable of executing program code. As one example, the data processing system may include organic components integrated with organic components and/or may be comprised entirely of organic components excluding a human being. For example, a storage device may be comprised of an organic semiconductor.

As another example, a storage device in data processing system 300 is any hardware apparatus that may store data. Memory 306, persistent storage 308 and computer readable media 318 are examples of storage devices in a tangible form.

In another example, a bus system may be used to implement communications fabric 302 and may be comprised of one or more buses, such as a system bus or an input/output bus. Of course, the bus system may be implemented using any suitable type of architecture that provides for a transfer of data between different components or devices attached to the bus system.

Additionally, a communications unit may include one or more devices used to transmit and receive data, such as a modem or a network adapter. Further, a memory may be, for example, memory 306 or a cache such as found in an interface and memory controller hub that may be present in communications fabric 302.

The different advantageous embodiments recognize that the use of ultrasonic signals such as, for example, Lamb waves, for non-destructive acoustic inspection of aircraft structures is an important tool for detecting and/or locating anomalies. A Lamb wave is a wave that propagates in a solid plate. The use of signals in the form of acoustic waves is capable of travelling through material in a structure with only nominal attenuation. Further, these types of signals may be sensitive to various types of anomalies that may occur within a structure.

The different advantageous embodiments, however, recognize that wave propagation through structures that may have a plate-like architecture is dispersive. In other words, the propagation of the signal is the sum of a number of signals, each of which may be generated by a separate mechanical mode that may be determined by the geometry of the structure.

In turn, each of these signals travels at a separate speed. This type of propagation of a signal may result in ambiguous signal information. The interpretation of this type of response also provides a significant technical challenge. The dispersion and multi-mode characteristics may limit the utility of using signals for identifying anomalies or changes in different types of aircraft structures.

The different advantageous embodiments provide a method, apparatus, and computer usable program code for processing a signal. In these examples, the signals are acoustic signals that may be Lamb waves. A response signal is received from the structure. The response signal is decomposed into a plurality of signals based on a number of characteristics. A mode is identified from the plurality of signals based on a number of known characteristics for the mode. In these examples, the mode has a velocity.

An estimate of the location of an anomaly may be identified based on a location of the mode within the response signal. In these examples, the time delay of the mode within the response signal may be used to identify a location by multiplying that time delay by the velocity. As used herein, a number of items refers to one or more items. For example, a number of characteristics is one or more characteristics.

Figure 4:
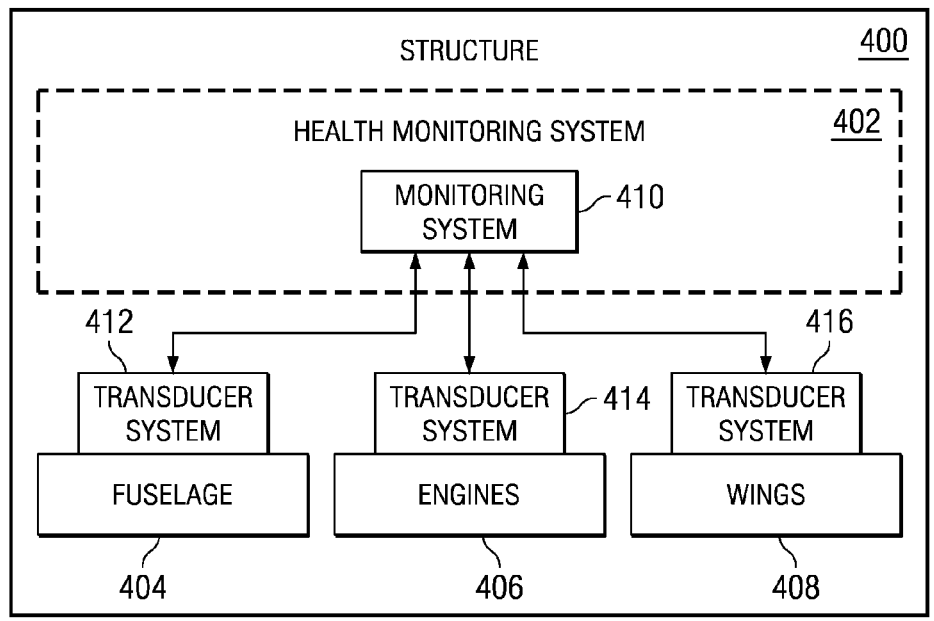
FIG. 4 is a diagram illustrating components used for structural health monitoring in a structure in accordance with an advantageous embodiment.

Turning now to FIG. 4, a diagram illustrating components used for a structural health monitoring system in a structure is depicted in accordance with an advantageous embodiment. Structure 400 is an example of a structure in which health monitoring system 402 may be implemented. Structure 400 may take many forms, such as, for example, an aircraft, a car, a tank, a ship, a submarine, a spacecraft, a dam, a building, a bridge, or some other suitable structure.

In this example, structure 400 takes the form of an aircraft. Structure 400 includes fuselage 404, engines 406, and wings 408. Other components also may be found in structure 400, but only these depicted ones are presented for purposes of illustrating different features in the different advantageous embodiments.

Health monitoring system 402 in structure 400 includes monitoring system 410, transducer system 412, transducer system 414, and transducer system 416. Although transducers are used for transmitters and sensors, in these examples, any type of transmitter, sensor, or device that is capable of sending and detecting signals at the frequencies needed to transmit the signals into a material may be used.

Monitoring system 410 may be implemented in structure 400 using a data processing system, such as data processing system 300 in FIG. 3. Monitoring system 410 may take the form of software, hardware, or a combination of software and hardware. In this example, monitoring system 410 is implemented in software using a data processing system, such as data processing system 300 in FIG. 3.

Transducer systems 412, 414, and 416 are examples of transmitters and sensors that may be implemented in structure 400 to transmit signals and detect responses to those signals. In these examples, the transducers in these systems are "associated" with the particular components in structure 400. A transmitter or sensor, such as those in transducer systems 412, 414, and 416, may be physically associated with the component by being attached to the component or even embedded within the component. In these examples, the transducers are fixed transmitters and fixed sensors that are not moved once they are placed.

In this depicted example, transducer system 412 is a set of one or more transducers that is placed onto or within fuselage 404. Transducer system 412 may be attached to surfaces within fuselage 404 or may be embedded into the materials itself, depending on the particular implementation.

The different transducers within transducer system 412 are arranged to be capable of monitoring one or more areas within fuselage 404. These areas may be selected based on different factors, such as identifying areas in which damage may cause a failure within fuselage 404. In a similar fashion, transducer system 414 is attached to or integrated with components in engines 406. Transducer system 416 also is integrated and configured to collect data from one or more areas in wings 408.

Transducer systems 412, 414, and 416 are controlled by monitoring system 410. Monitoring system 410 may send signals for transmission by these transducer systems. Further, the responses received in response to these signals are returned to monitoring system 410 for processing. The responses collected from transducer systems 412, 414, and 416 are compared to baseline or comparison signals.

The illustration of structure 400 in FIG. 4 is presented for the purposes of explaining one advantageous embodiment. This illustration is not meant to limit the manner in which different advantageous embodiments may be implemented or embodied. For example, in other advantageous embodiments, other numbers of transducer systems may be present. For example, structure 400 may include five, ten, twenty, or some other suitable number of transducer systems depending on the particular implementation. Also, additional structural health monitoring systems, in addition to health monitoring system 402, also may be present for redundancy.

Figure 5:
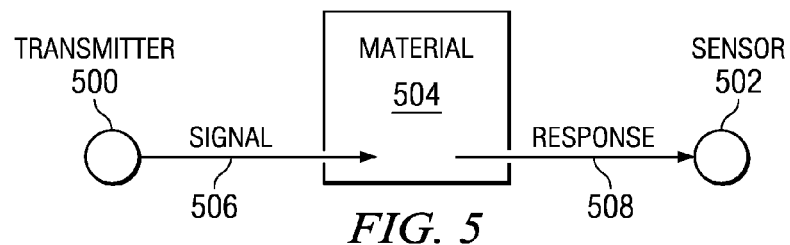
FIG. 5 is a diagram illustrating signal transmission and detection in accordance with an advantageous embodiment.

Turning now to FIG. 5, a diagram illustrating signal transmission and detection is depicted in accordance with an advantageous embodiment. In this example, transmitter 500 and sensor 502 may be used to test material 504. Transmitter 500 and sensor 502 are examples of a transmitter and sensor that may be found in transducer system 412 in FIG. 4. Material 504 is an example of a material that may be present in a structure, such as fuselage 404 or wings 408 in FIG. 4.

Transmitter 500 transmits or sends signal 506 into material 504. Signal 506 is a waveform having a selected frequency range. Response 508 is detected by sensor 502. Response 508 is generated in response to the transmission of signal 506 into material 504. Although in this example, sensor 502 is shown as receiving response 508 on an opposite side of material 504 from transmitter 500, sensor 502 may be located on the same side of material 504 as transmitter 500. With this configuration, response 508 is detected from reflections or scattering of signal 506 being transmitted into material 504.

Response 508 is used, in these different illustrative examples, in a comparison with a prior response to determine whether changes have occurred in material 504. These changes may be anomalies that occur through various stresses and other environmental conditions to which material 504 is subjected over time.

Figure 6:
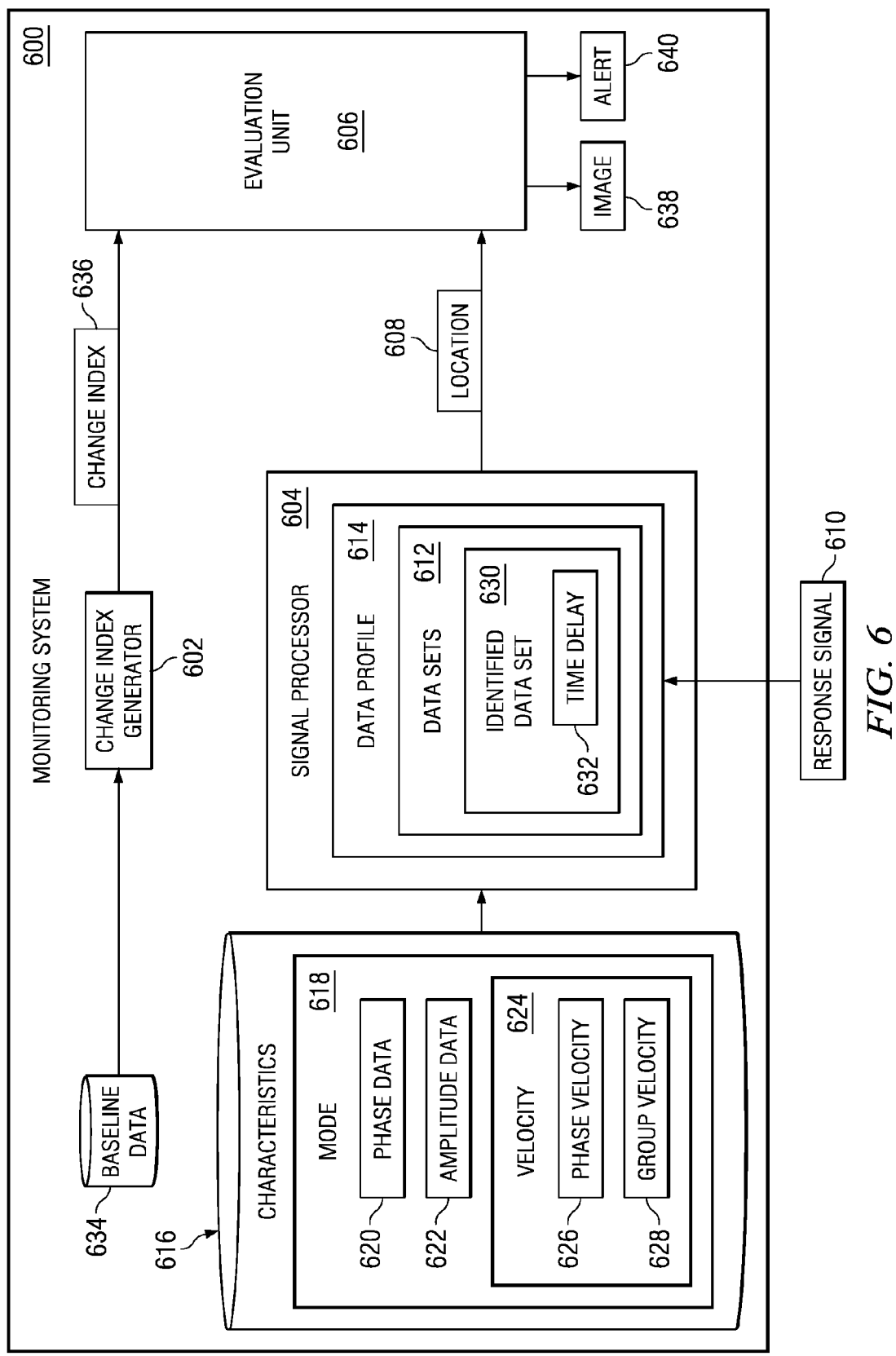
FIG. 6 is a diagram of a monitoring system in accordance with an advantageous embodiment.

With reference now to FIG. 6, a diagram of a monitoring system is depicted in accordance with an advantageous embodiment. In this example, monitoring system 600 is an example of one implementation for monitoring system 410 in FIG. 4. As illustrated, monitoring system 600 includes change index generator 602, signal processor 604, and evaluation unit 606.

Signal processor 604 generates location 608 by processing response signal 610. Response signal 610 is broken down and/or decomposed into data sets 612. In separating response signal 610 into data sets 612, constraints may be used to make the separations. T These constraints may include, for example, phase, higher order phase rates, group delay estimates, width and/or shape of the amplitude envelopes for the modes of response signal 610, frequency, and/or cycles contained in the amplitude envelope for response signal 610. In these examples, response signal 610 may take the form of a chirp. In these illustrative examples, a chirp is a signal with a property in which the signal has a frequency that varies linearly or nonlinearly in time.

These data sets form data profile 614. The data sets may include information such as, for example, phase information and amplitude information. Each data set from data sets 612 may be a potential mode. Some of the data sets may not form modes depending on response signal 610.

Signal processor 604 processes data profile 614 by comparing data profile 614 to characteristics 616. Characteristics 616 take the form of dispersion characteristics in these examples. Dispersion characteristics are the parametric relationships that exist between frequency, phase and group velocities inherent to an acoustic wave.

Each mode in an acoustic wave has a unique set of dispersion characteristics which are determined by one of a discrete number of vibration states, which are mechanically excited in that structure. These vibration states may be determined by the material and geometric properties of the structure in which the wave is traveling. Characteristics 616 contain characteristics for modes such as mode 618.

In these different illustrative embodiments, a mode is a portion of a signal that propagates with a particular set of characteristics. For example, a mode may be a particular wave that travels with a different speed and frequency from other waves that make up a signal. A summation of all the different modes forms response signal 610.

In this example, mode 618 may be identified with phase data 620 and/or amplitude data 622. Mode 618 also has velocity 624. Velocity 624 may include at least one of phase velocity 626 and/or group velocity 628. As used herein, the phrase "at least one of", when used with a list of items, means that different combinations of one or more of the items may be used and only one of each item in the list may be needed. For example, "at least one of item A, item B, and item C" may include, for example, without limitation, item A or item A and item B. This example also may include, item A, item B, and item C, or item B and item C.

In these examples, group velocity 628 is used to estimate location 608. Group velocity 628 is a velocity at which variations in the shape of the amplitude of a wave propagate through a structure or space. Group velocity is often thought of as the velocity at which energy or information may be conveyed along a wave. Group velocity 628 also may be referred to as a signal velocity for the waveform.

In comparing phase data 620 and/or amplitude data 622 to corresponding data within data profile 614, a best fit is made with this data to identify a particular data set within data sets 612 in data profile 614. In this example, the identified data is identified data set 630.

Identified data set 630 has time delay 632. This time delay is used with group velocity 628 and velocity 624 to generate location 608. With just response signal 610, location 608 is an estimated location. Location 608 may become more accurate with additional response signals such as, for example, response signal 610 being processed by signal processor 604.

For example, signal processor 604 may generate a signal or waveform for mode 618 in characteristics 616 using phase data 620 and amplitude data 622 to make a comparison with data sets 612 in data profile 614. Signal processor 604 may subtract identified data set 630 from data sets 612. The remaining data sets in data sets 612 form residual sets from which additional identifications of modes may be made. Signal processor 604 may generate another mode from other data in characteristics 616 to identify additional matching data within data profile 614. In some cases, more than one mode may be identified or located within data sets 612.

Additionally, response signal 610 also may be compared to baseline data 634 to generate change index 636. Baseline data 634 may take the form of signals generated in response to interrogating the structure at a prior point in time. These signals also may be referred to as comparison signals. The prior point in time may be a time when the structure was first manufactured or some other point in time after the creation of the structure.

Change index 636 and location 608 may be processed by evaluation unit 606. Evaluation unit 606 may generate image 638 and alert 640. Image 638 may be an image of a structure with identification of location 608 within the structure. Alert 640 may be a visual and/or audio alert presented on a user interface. In some advantageous embodiments, alert 640 may be a message sent to another data processing system or device. Alert 640 may indicate that maintenance or inspection may be needed at a later point in time or that some immediate action may be needed. Image 638 may aid in the inspection of the structure.

The illustration of monitoring system 600 is not meant to imply physical or architectural limitations to the manner in which different embodiments may be implemented. Other embodiments may have components in addition to or in place of the ones illustrated. Yet other embodiments may have fewer components. For example, in some advantageous embodiments, monitoring system 600 may not include change index generator 602. In yet other advantageous embodiments, characteristics 616 may be located in a database or file remote to monitoring system 600.

Figure 7:
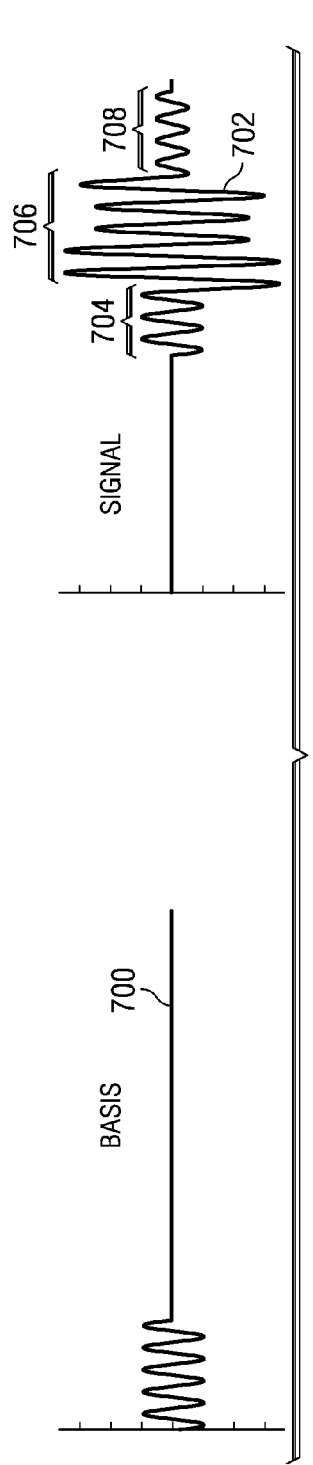
FIG. 7 is a diagram illustrating the decomposing of a reference signal in accordance with an advantageous embodiment.

With reference now to FIG. 7, a diagram illustrating the decomposing of a reference signal is depicted in accordance with an advantageous embodiment. In this example, basis signal 700 and response signal 702 are shown. In this example, response signal 702 includes mode 704, mode 706, and mode 708. The different modes illustrated for response signal 702 contain phase, higher order phase rates, group delay and amplitude data.

These characteristics, among other characteristics, are used to separate the different modes present in response signal 702 into different data sets. Basis signal 700 may be scaled, frequency ramped, and/or shifted to identify different modes within response signal 702. This scaling, frequency ramping, and/or shifting may be performed to match or approximate the form of a portion of response signal 702. Basis signal 700 may be generated from characteristics of a mode, such as, for example, characteristics 616 in FIG. 6.

Figure 8:
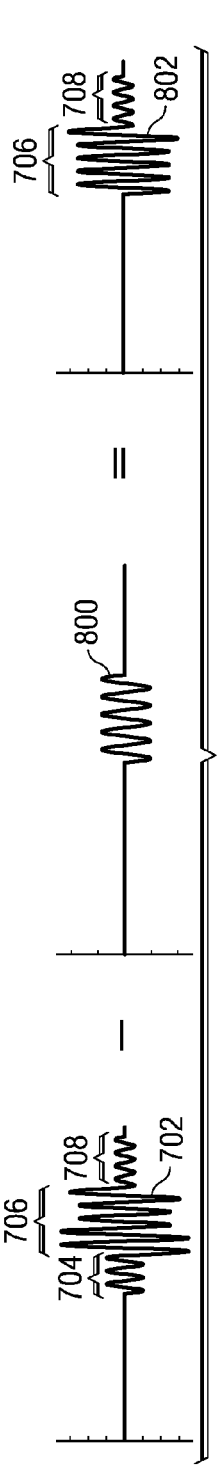
FIG. 8 is a diagram illustrating the decomposing of a reference signal in accordance with an advantageous embodiment.

In FIG. 8, basis signal 800 has phase, higher order phase rates, and group delay and amplitude data that matches the equivalent characteristic data from mode 704. Basis signal 800 is subtracted from response signal 702. Basis signal 800 is a scaled, frequency ramped and/or shifted version of basis signal 700 and corresponds to mode 704 of response signal 702. This signal is a simpler signal as compared to response signal 702. This subtraction of basis signal 800 from response signal 702 results in signal 802.

Figure 9:
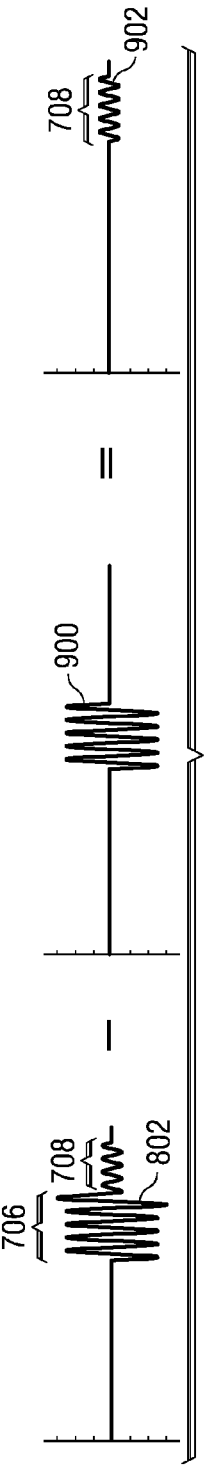
FIG. 9 is a diagram illustrating the decomposing of a reference signal in accordance with an advantageous embodiment.
Figure 10:
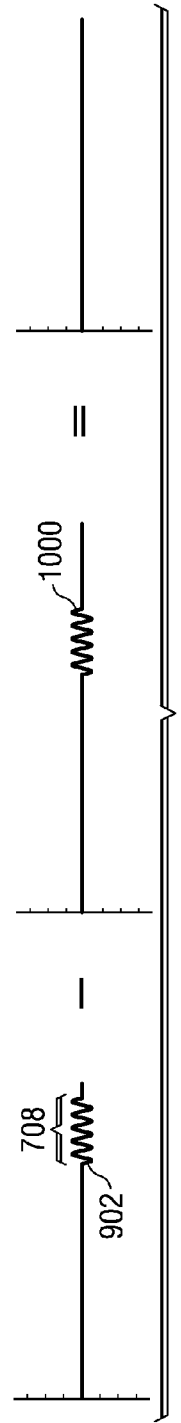
FIG. 10 is a diagram illustrating the decomposing of a reference signal in accordance with an advantageous embodiment.

In FIG. 9, basis signal 900 is formed from characteristics of a desired mode. Basis signal 900 has phase, higher order phase rates, and group delay and amplitude data that match the equivalent characteristic data from mode data for mode 706 within response signal 702. Basis signal 900 is subtracted from signal 802 to form signal 902. Basis signal 900 corresponds to mode 706 of response signal 702 in these examples. In FIG. 10, signal 1000 is formed from characteristics of another desired mode.

Basis signal 1000 has phase, higher order phase rate, and group delay and amplitude data that match the equivalent characteristic data from mode 708 within response signal 702. Basis signal 1000 is subtracted from signal 902 with no portion of response signal 702 remaining. Basis signal 1000 corresponds to mode 708 of response signal 702.

Basis signals 800, 900, and 1000 form the signals for the different modes of response signal 702 in FIG. 7. These signals may be summed to reform an approximation of response signal 702. In this example, only three modes are illustrated for purposes of depicting one manner in which a decomposition process may occur. In other advantageous embodiments, other modes may be obtained from the response signal. For example, twenty modes, thirty modes, or some other suitable number of modes may be selected. A similar process may be performed for the comparison signals, as well as the reference signals.

The group delay is a frequency-dependent quantity that measures the average time of arrival of each frequency contained in a time localized signal, which traverses a known distance. The group delay is also the known distance traversed divided by the group velocity.

Figure 11:
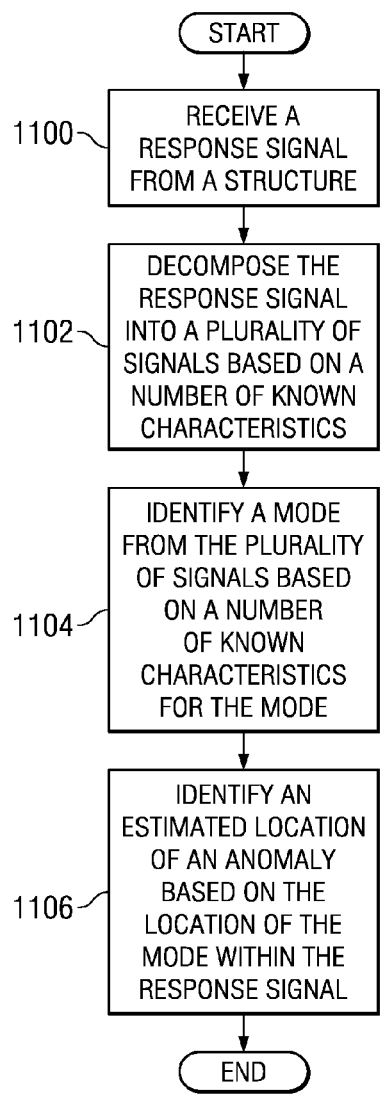
FIG. 11 is a high level flowchart of a process for processing a signal in accordance with an advantageous embodiment.

With reference now to FIG. 11, a high level flowchart of a process for processing a signal is depicted in accordance with an advantageous embodiment. The process illustrated in FIG. 11 may be implemented in a monitoring system such as, for example, monitoring system 600 in FIG. 6. The process may be implemented as a software component such as, for example, signal processor 604 within monitoring system 600 in FIG. 6.

The process begins by receiving a response signal from a structure (operation 1100). The process then decomposes the response signal into a plurality of signals based on a number of known characteristics (operation 1102). This decomposition of the signal may be performed by grouping characteristics in the response signal.

A mode is identified from the plurality of signals based on a number of known characteristics for the mode (operation 1104). In this example, the known mode or desired mode has a velocity. This velocity takes the form of a group velocity in these examples. The process then identifies an estimated location of an anomaly based on the location of the mode within the response signal (operation 1106) with the process terminating thereafter.

Figure 12:
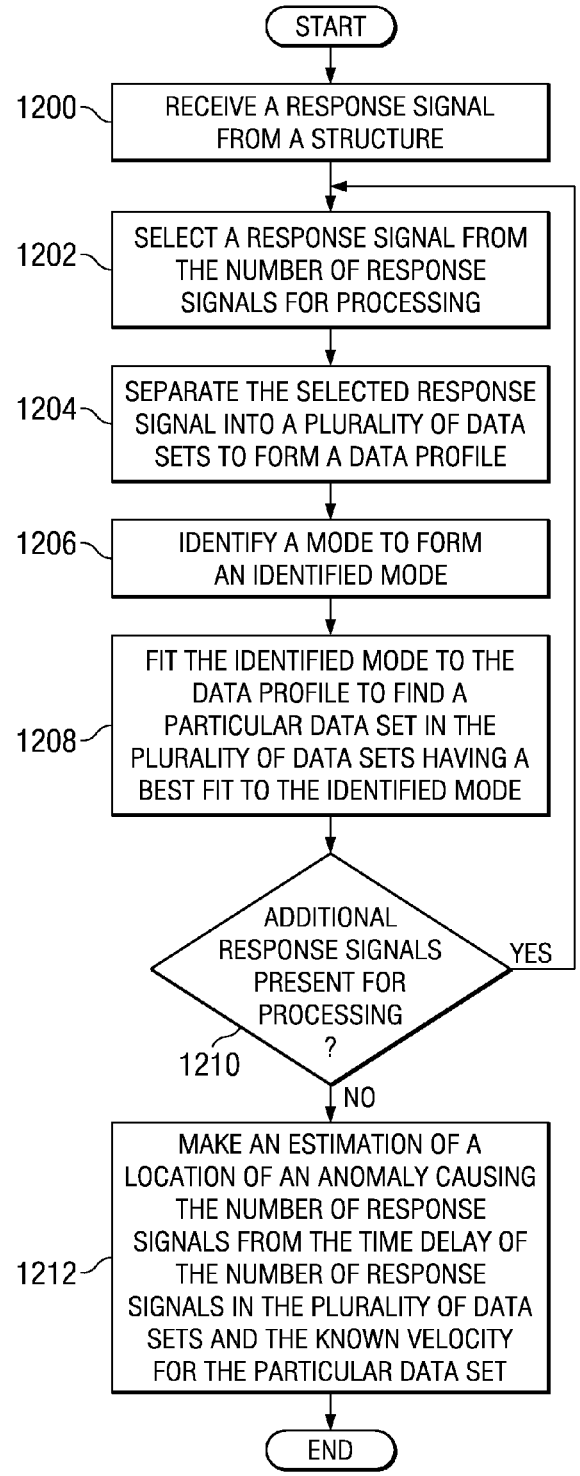
FIG. 12 is a flowchart of a process for processing a signal in accordance with an advantageous embodiment.

With reference now to FIG. 12, a flowchart of a process for processing a signal is depicted in accordance with an advantageous embodiment. The process illustrated in FIG. 12 may be implemented in a monitoring system such as, for example, monitoring system 600 in FIG. 6. More specifically, the process may be implemented in a software component such as, for example, signal processor 604 within monitoring system 600 in FIG. 6.

The process begins by receiving a response signal from a structure (operation 1200). The response signal is generated in response to a signal being sent into the structure by a transducer. The process then selects a response signal from the number of response signals for processing (operation 1202).

The process then separates the selected response signal into a plurality of data sets to form a data profile (operation 1204). In operation 1204, the separating of the response signal into data sets may be performed using the following equations in the time domain:

$$S(t) \cong \sum_i S_i(t)$$

-continued
$$S_i(t) = \exp(Z_{2i}t^2 + Z_{1i}t + Z_{0i}); \text{ where: } \text{real}(Z_{2i}) < 0$$

where S(t) is an approximation of the selected response, an each $S_i(t)$ is a basis function, such as the examples referred to in FIG. 7. The quantities $Z_{2i}$, $Z_{1i}$, $Z_{0i}$ are complex numbers, which are curve fit parameters of the basis function. Each parameter is a composite function of amplitude, initial phase, center frequency, and chirp rate. The parameter t is time.

Since phase and amplitude characteristics are contained in Z parameters, the complex Z's may be computed by performing a constrained least squares fit on the signal data. The constraints on the parameters are the same constraints referred to in the description of FIG. 6. A frequency domain decomposition may be performed in a similar fashion and applied to a Fourier transformed response signal.

The signal may also be transformed into the time-frequency or time-scale domains using a number of well known transforms, Short Time Fourier, Wigner-Ville, Wavelet transforms, or other suitable transforms. For example, a short time Fourier transformed signal can be separated into different transformed data sets using the following two-dimensional basis:

$$S(t, \omega) \cong \sum_i S_i(t, \omega)$$

$$S_i(t, \omega) = \exp(Z_{20i}t^2 + Z_{02i}\omega^2 + Z_{10i}t + Z_{01i}\omega + Z_{11i}t\omega + Z_{00i});$$

$$\text{real}(Z_{20i}) < 0$$

In this case, S(t, ω) is an approximation of the Short Time Fourier Transform of the selected response where each $S_i(t, \omega)$ is an example of two-dimensional time-frequency basis function. The quantities $Z_{20i}$, $Z_{02i}$, $Z_{10i}$, $Z_{01i}$, $Z_{11i}$, and $Z_{00i}$ are complex numbers which are surface fit parameters of the two-dimensional basis function. Each parameter is a composite function of amplitude, initial phase, center frequency, chirp rate, and center group delay. The parameters ω and t are frequency and time respectively, and i is a parameter that indexes each basis function.

In this example, all phase and amplitude information is in the Z parameters. The complex Z's are computed by performing a constrained least squares surface fit on time frequency image data. Least squares data sets may be centered at a local image or signal maxima.

Following operation 1204, the process then identifies a mode to form an identified mode (operation 1206). In these examples, the identified mode may be, for example, mode 618 in FIG. 6. This identified mode has a data set and a known group velocity. The data set may include additional characteristic data about the identified mode. The process then fits the identified mode to the data profile to find a particular data set in the plurality of data sets having a best fit to the identified mode (operation 1208).

A determination is then made as to whether additional response signals are present for processing (operation 1210). If additional response signals are present, the process returns to operation 1202. Otherwise, an estimation of a location of an anomaly causing the number of response signals is made from the time delay of the number of response signals in the plurality of data sets and the known velocity for the particular data set (operation 1212), with the process terminating thereafter. This particular data set has a group velocity that is known because the data set matches the identified mode.

Figure 13:
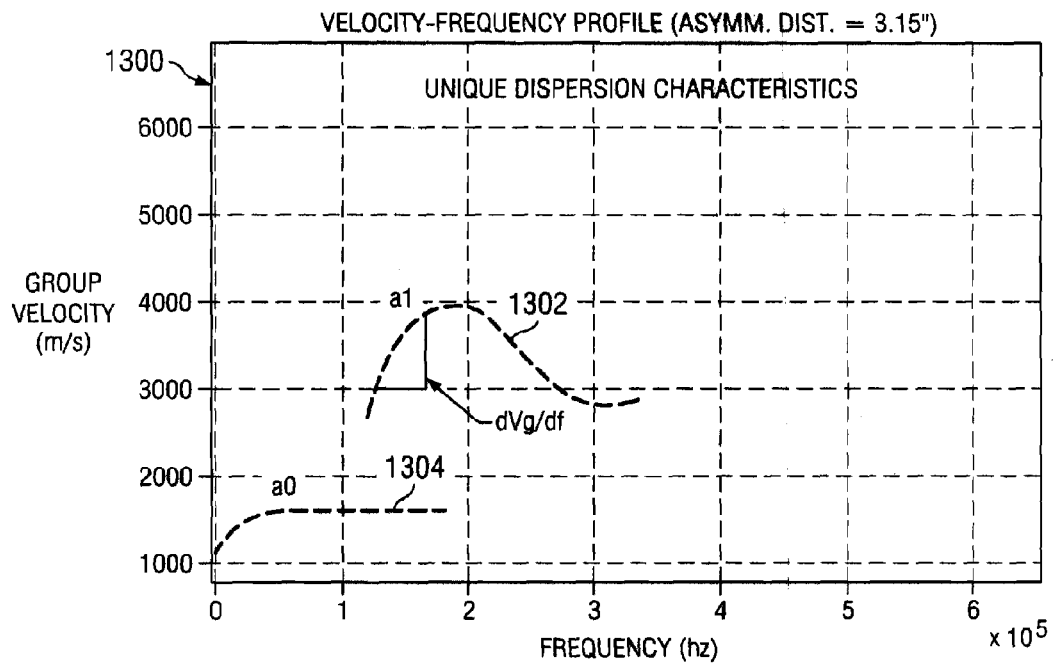
FIG. 13 is a diagram illustrating dispersion curves in accordance with an advantageous embodiment.

With reference now to FIG. 13, a diagram illustrating dispersion curves is depicted in accordance with an advantageous embodiment. Graph 1300 illustrates dispersion curves for mode 1302 and mode 1304. In this example, the Y axis represents group velocity, while the X axis represents frequency. In this illustrative example, mode 1302 may correspond to a front scatter, while mode 1304 corresponds to a back scatter from an anomaly. These two modes have been generated in response to a signal encountering an anomaly within a structure.

As can be seen, each mode has a characteristic group velocity for different frequencies. The amplitude data and phase data in the data sets for mode 1302 and mode 1304 may form the data sets for use in identifying a desired mode. Characteristic data from a desired mode may be compared to these modes in graph 1300 to determine whether either mode 1302 or mode 1304 matches or provides a best fit to the desired mode.

Figure 14:
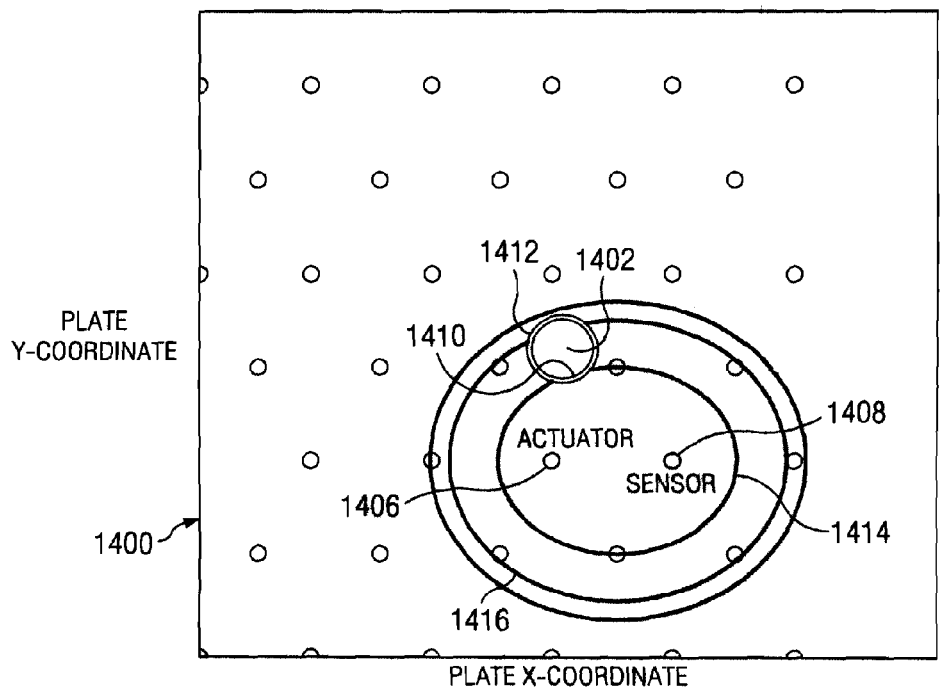
FIG. 14 is a diagram illustrating an estimation of a location for an anomaly in accordance with an advantageous embodiment.

With reference now to FIG. 14, a diagram illustrating an estimation of a location for an anomaly is depicted in accordance with an advantageous embodiment. In this example, structure 1400 contains anomaly 1402. Actuator 1406 transmits a signal into structure 1400, while sensor 1408 detects a response to the signal.

Actuator 1406 may generate two waves when actuator 1406 sends a signal into structure 1400 that encounters anomaly 1402. In this example, the front scatter is caused by point 1410 of anomaly 1402. Point 1410 is a point on anomaly 1402 closest to sensor 1408. The back scatter is caused by point 1412 of anomaly 1402. Point 1412 is on a back side of anomaly 1402 or a side opposite to sensor 1408.

In these examples, the front scatter wave caused by point 1410 may be used to generate estimated location 1414. Estimated location 1414 is a circle and/or ellipse. The back scatter wave may be used to generate estimated location 1416. The difference between these two locations may be used to estimate a size of anomaly 1402. With data from additional transmitters and sensors, overlaps between the circles or ellipses may be used to identify a more precise estimated location for anomaly 1402. This type of mechanism requires less transmitters and sensors than in currently used triangulation methodologies. Further, with the back scatter and front scatter waves, a size of delamination also may be identified.

Figure 15:
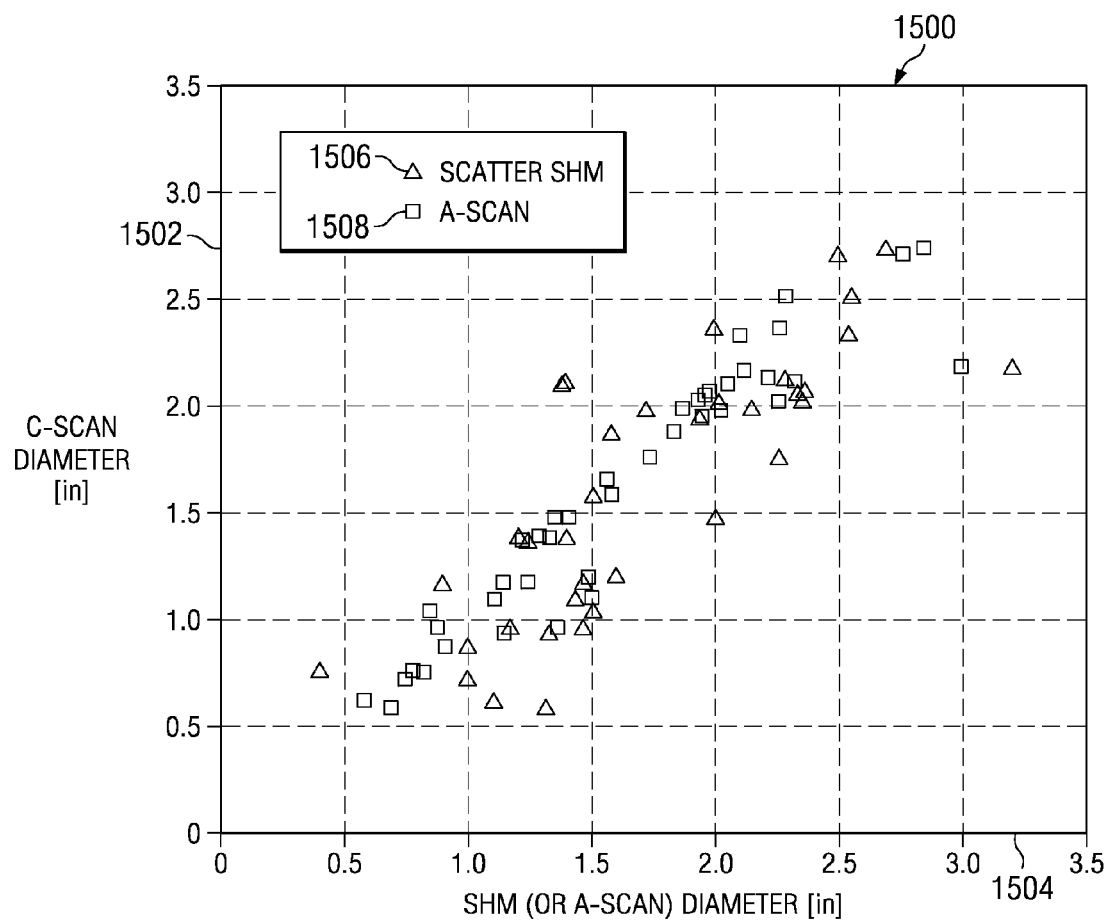
FIG. 15 is a diagram illustrating anomaly sizing results in accordance with an advantageous embodiment.

With reference now to FIG. 15, a diagram illustrating anomaly sizing results is depicted in accordance with an advantageous embodiment. In this example, graph 1500 shows C-scan diameter results in inches on Y axis 1502. X axis 1504 illustrates diameter results from a scan using both conventional health monitoring systems and one in accordance with an advantageous embodiment.

As can be seen, results 1506 are generated with mode decomposition and processing as described above. Results 1508 are ones obtained from a conventional ultrasound health monitoring system.

Thus, the different advantageous embodiments provide a method, apparatus, and computer program product for processing signals. In the different advantageous embodiments, a response signal is received from a structure. This response signal may be decomposed into a plurality of signals based on a number of characteristics. A mode in the plurality of signals may be identified based on a number of known characteristics for the mode. This mode has a velocity. With this information, an estimated location of an anomaly may be identified based on the location of the mode within the response signal.

One or more modes may be identified within the response signal and used to identify whether anomalies may be present within the structure.

Each mode within a signal may be associated or cross-correlated with a scatter signal that may be caused by an anomaly. With the presence of estimated group velocities, the peaks of these cross-correlation functions correspond to time delay as well as likely travel distances from the actuator to the anomaly and then to the sensor. In other words, the time delay may be used to obtain the distance from the transmitter to the anomaly and then to the sensor.

In this manner, the number of sensors and transmitters needed in a structure may be reduced based on the manner in which anomalies may be located. Further, manual processing and validation of large sets of data to estimate group velocities of signals in response to structures may be reduced through this process.

The different advantageous embodiments can take the form of an entirely hardware embodiment, an entirely software embodiment, or an embodiment containing both hardware and software elements. Some embodiments are implemented in software, which includes, but is not limited to, forms, such as, for example, firmware, resident software, and microcode.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution system, apparatus, or device.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems or remote printers or storage devices through intervening private or public networks. Non-limiting examples are modems and network adapters and are just a few of the currently available types of communications adapters.

The description of the different advantageous embodiments has been presented for purposes of illustration and description and is not intended to be exhaustive or limited to the embodiments in the form disclosed. Many modifications and variations will be apparent to those of ordinary skill in the art. Further, different advantageous embodiments may provide different advantages as compared to other advantageous embodiments.

The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for processing a signal in a structure, the method comprising:
    receiving a response signal from a structure;
    decomposing the response signal into a plurality of signals based on a number of characteristics;
    identifying a first mode in the plurality of signals based on a number of known characteristics for the first mode to obtain an identified mode, wherein the identified mode has a velocity, the velocity comprising a group velocity and a phase velocity, the group velocity comprising a velocity at which variations in a shape of an amplitude of a wave propagate through the structure;
    fitting a data set for the identified mode so as to form an identified data set;
    subtracting the identified data set from a plurality of data sets to form residual data sets;
    identifying a second mode in the residual data sets; and
    identifying an estimated location of an anomaly based on a location from data of the first mode and the second mode within the response signal.

2. The method of claim 1, wherein the velocity is a group velocity and wherein the location of the first mode within the response signal is a time delay and wherein the identifying step comprises:
    multiplying the group velocity by the time delay to obtain a distance; and
    estimating the estimated location of the anomaly using the distance.

3. The method of claim 2 further comprising:
    identifying the location of the first mode within the response signal;
    identifying a time delay of the first mode; and
    estimating the estimated location of the anomaly using the time delay and the velocity.

4. The method of claim 1, wherein the response signal is a first response signal and further comprising:
    receiving a second response signal from the structure;
    decomposing the second response signal into a second plurality of signals based on a second number of known characteristics; and
    identifying a third mode from the second plurality of signals based on the number of known characteristics for the third mode from the second plurality of signals; and
    identifying an estimated location for an anomaly based on a first location of the first mode within the first response signal and a second location for the third mode in the second response signal.

5. The method of claim 1, wherein the decomposing step comprises:
    separating the response signal into a plurality of data sets to form a data profile.

6. The method of claim 5, wherein the plurality of data sets comprises phase data, amplitude data, phase rate data, and group delay data.

7. The method of claim 6, wherein the identifying a first mode step comprises:
    identifying a particular data set within the data profile having a best fit to a known data set for the first mode, and wherein the data profile comprises dispersion characteristics from a dispersion curve.

8. The method of claim 1, wherein the signal is a chirp signal.

9. The method of claim 1, wherein identifying a second mode further comprises:
    identifying another mode from the plurality of signals based on another number of characteristics for the another mode, wherein the another mode has another velocity.

10. The method of claim 1, wherein the structure is selected from one of a mobile platform, a stationary platform, a land-based structure, an aquatic-based structure, a space-based structure, an aircraft, a surface ship, a tank, a personnel carrier, a train, a spacecraft, a submarine, an automobile, a power plant, a bridge, a dam, a manufacturing facility, and a building.

11. A method for processing a signal to estimate a location of an anomaly, the method comprising:
    receiving a response signal from a structure, wherein the response signal is generated in response to the signal being sent into the structure by a transducer;
    separating the response signal into a plurality of data sets to form a data profile, the plurality of data sets comprising at least one of phase data and amplitude data;
    identifying a mode to form an identified mode, wherein the identified mode comprises a data set and a known group velocity for a first scatter pattern related to a first point of the anomaly;
    fitting the data set for the identified mode to the data profile to find a particular data set having a best fit to the identified mode so as to form an identified data set;
    subtracting the identified data set from the plurality of data sets to form residual data sets;
    identifying a second mode to form a second identified mode, wherein the second identified mode comprises a data set and a known group velocity for a second scatter pattern related to a second point of the anomaly;
    fitting the data set for the second identified mode to the data profile in the residual data sets to find a particular data set having a best fit to the second identified mode;
    estimating a location of the first point and a location of the second point so as to estimate a size of the anomaly; and
    estimating the location of the anomaly causing the response signal from a time delay of the data set and the known group velocity for the data set of the first mode and from a time delay of the data set and the known group velocity for the data set of the second mode.

12. The method of claim 11, wherein the identified mode signal is a chirp.

13. The method of claim 11, wherein the structure is selected from one of a mobile platform, a stationary platform, a land-based structure, an aquatic-based structure, a space-based structure, an aircraft, a surface ship, a tank, a personnel 14. An apparatus comprising:
- a structure having a plurality of components;
- a number of transmitters physically associated with the plurality of components, wherein the number of transmitters is capable of sending signals into the plurality of components;
- a number of sensors physically associated with the plurality of components, wherein the number of sensors is capable of detecting responses to the signals;
- a structural health monitoring system in communication with the number of transmitters and the number sensors, wherein the structural health monitoring system is capable of causing a transmitter in the number of transmitters to send a signal into a component within the plurality of components; receiving a response signal generated in response to the signal; decomposing the response signal into a plurality of signals based on a number of characteristics;
- identifying a first mode within the plurality of signals based on a number of known characteristics for the first mode, wherein the first mode has a velocity, the velocity comprising a group velocity and a phase velocity, the first mode corresponding to a first scatter pattern related to a first point of the anomaly; fitting a data set for the first mode so as to form an identified data set; subtracting the identified data set from a plurality of data sets to form residual data sets; identifying a second mode in the residual data sets within the plurality of signals based on a number of known characteristics for the second mode, wherein the second mode has a velocity, the velocity comprising a group velocity and a phase velocity, the second mode corresponding to a second scatter pattern related to a second point; estimating a location of the first point and a location of the second point so as to estimate a size of an anomaly; and identifying an estimated location of the anomaly based on a location from data of the first mode and the second mode within the response signal.

15. The apparatus of claim 14, wherein the structural health monitoring system identifies an estimated location of an anomaly within the component based on a location of the first mode within the response signal.

16. The apparatus of claim 14, wherein the number of transmitters and the number of sensors are a number of transducers.

17. The method of claim 14, wherein the structure is selected from one of a mobile platform, a stationary platform, a land-based structure, an aquatic-based structure, a space-based structure, an aircraft, a surface ship, a tank, a personnel carrier, a train, a spacecraft, a submarine, an automobile, a power plant, a bridge, a dam, a manufacturing facility, and a building.

18. A non-transitory computer readable medium encoded with a computer program product for processing a signal and estimating a location of an anomaly in an aircraft, the computer program product comprising:
- program code for receiving a response signal from an aircraft;
- program code for decomposing the response signal into a plurality of signals based on a number of characteristics; and
- program code for identifying a first mode in the plurality of signals based on a number of known characteristics for the first mode, wherein the first mode is characterized by a plurality of velocities, one velocity comprising a group velocity and a second velocity comprising a phase velocity, the first mode corresponding to a first scatter pattern related to a first point of the anomaly;
- program code for fitting a data set for the identified first mode so as to form an identified data program code for subtracting the identified data set from a plurality of data sets to form residual data sets;
- program code for identifying a second mode in the residual data sets in the plurality of signals based on a number of known characteristics for the second mode, wherein the second mode is characterized by a plurality of velocities, one velocity comprising a group velocity and a second velocity comprising a phase velocity, the second mode corresponding to a second scatter pattern related to a second point;
- program code for estimating a location of the first point and a location of the second point so as to estimate a size of an anomaly; and
- program code for identifying an estimated location of an anomaly on the aircraft based on a location from data of the first mode and the second mode within the response signal.

* * * * *